United States Patent [19]

Dreux et al.

[11] Patent Number: 4,785,007

[45] Date of Patent: Nov. 15, 1988

[54] DRUGS COMPRISING 2,3- OR 3,4-DIPHENYL DERIVATIVES OF γ-NITRILE-ESTERS OR THE CYCLIZATION PRODUCTS THEREOF

[75] Inventors: Jacques Dreux, Lyons; Serge Petit, Villeurbanne, both of France

[73] Assignee: Laboratoires Hoechst S.A., Puteaux, France

[21] Appl. No.: 847,255

[22] Filed: Apr. 2, 1986

[30] Foreign Application Priority Data

Apr. 4, 1985 [FR] France ................. 85 05123

[51] Int. Cl.$^4$ .......................... A61K 31/445
[52] U.S. Cl. .................................. 514/327
[58] Field of Search ........................ 514/327

[56] References Cited

U.S. PATENT DOCUMENTS

| | | | |
|---|---|---|---|
| 3,468,893 | 9/1969 | Mizzoni | 260/293 |
| 3,718,743 | 2/1973 | Shen et al. | 424/267 |
| 3,814,771 | 6/1974 | Shen et al. | 260/293.73 |
| 3,956,314 | 5/1976 | Strubbe et al. | 260/326.5 FL |

FOREIGN PATENT DOCUMENTS 0001601 5/1979 European Pat. Off. .
765203 8/1939 Fed. Rep. of Germany .

OTHER PUBLICATIONS

Chem. Abst. vol. 69-10,3332, (1968).
Mortimer Aust. J. Chem., 21, 1968, pp. 467–476.

*Primary Examiner*—Stanley J. Friedman
*Attorney, Agent, or Firm*—Finnegan, Henderson, Farabow, Garrett and Dunner

[57] ABSTRACT

New drugs comprising 2,3- or 3,4-diphenyl derivatives of γ-nitrile-esters or the products of cyclization of the 2,3-diphenyl derivatives according to the formulae A, B and C are claimed.

Process for cyclization of 2,3-diphenyl derivatives of γ-nitrile-esters, new 2,3-diphenyl derivatives of γ-nitrile-esters corresponding to the formulae I to VIII are claimed; new 3,4-diphenyl derivatives of the said esters coresponding to the formulae IX and X, and new 3,4-diphenylpiperidone derivatives corresponding to the specific formulae IX to XXVII are described.

5 Claims, No Drawings

DRUGS COMPRISING 2,3- OR 3,4-DIPHENYL DERIVATIVES OF γ-NITRILE-ESTERS OR THE CYCLIZATION PRODUCTS THEREOF

The present invention relates to new drugs comprising 2,3-or 3,4-diphenyl derivatives of γ-nitrile-esters or the cyclization products thereof, to new 2,3- and 3,4-diphenyl derivatives of γ-nitrile-esters and the cyclization products thereof, to processes for preparing them and to their use as drugs, preferably for the treatment of acute and chronic renal insufficiency (nitrile-esters) and for psychostimulants and antidepressants.

A few references are found in the literature relating to the 2,3- or 3,4-diphenyl series of γ-nitrile-esters [cf. in particular, the studies by:

C. F. KOELSCH, J. A. C. S., 65, 437-9 (1943)
POPANDOVA, K., IVANOV, K. H., God. Sofii. Univ. Khim. Fak. 1970-1971 (Pub. 1973), 65 252-260 (Bulg) as regards the 2,3-diphenyl derivatives, and the studies by
S. AVERY, J.A.C.S., 50, 2512-9 (1928)
C. F. KOELSCH, J.A.C.S., 65, 437-9 (1943)
W. M. BARR et J. W. COOK, J. Chem. Soc., 438-41 (1945)
R. BERTOCCHIO and J. DREUX, Bull. Soc. Chim. Fr., 1809-13(1962).

as regards the 3,4-diphenyl derivatives, of γ-nitrile-esters].

Far fewer references are to be found as regards piperidones, that is to say the cyclization products of the said γ-nitrile-esters (for example MORTIMER in Aust. J. Chem., 21, 467-76, 1968).

The Applicant has found that these products, and many other new products, not previously described, which it has synthesized and which belong to the same family, were endowed with exceptional therapeutic properties.

The subject of the present invention is consequently new drugs which comprise 2,3- or 3,4-diphenyl derivatives of γ-nitrile-esters or the cyclization products of the 2,3-diphenyl derivatives and which correspond to the formulae A, B, and C below:

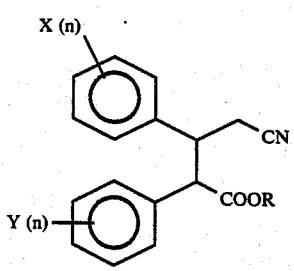

(A)

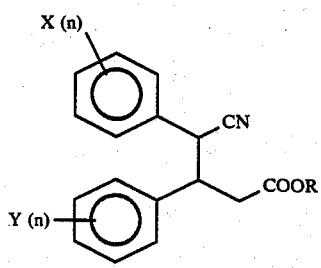

(B)

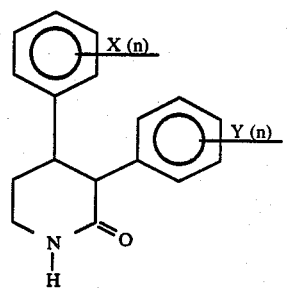

(C)

The formula A represents the 2,3-diphenyl-substituted γ-nitrile-esters,

The formula B represents the 3,4-diphenyl-substituted γ-nitrile-esters,

The formula C represents the cyclization products of the 2,3-diphenyl-substituted γ-nitrile-esters, in which formulae, R denotes a hydrogen atom or a pharmaceutically compatible alkali metal or alkaline-earth metal or a $C_1$–$C_4$ alkyl group, and X or Y, which may be identical or different, denote a hydrogen or halogen atom or a $C_1$–$C_4$ alkyl, $C_1$–$C_4$ alkoxy, phenyl, phenyl-($C_1$–$C_4$ alkyl) or trifluoromethyl group in the formulae A and B, and in which X or Y, which may be identical or different, denotes a hydrogen or halogen atom or a trifluoromethyl, $C_1$–$C_4$ alkyl, phenyl, phenyl-($C_1$–$C_4$ alkyl), $C_1$–$C_4$ alkoxy, hydroxy, acyloxy, phenoxy, benzyloxy, $C_1$–$C_4$ alkylsulfonyl or di($C_1$–$C_4$ alkyl)amino group in the formula C, n being between 1 and 3 in the case where X and/or Y are other than hydrogen.

The products represented by the formulae A and B can be in the erythro or threo configuration, and cis or trans in the case of piperidones (formula C).

While the preparation of some of the abovementioned derivatives is described in the literature (this is the case, in particular, for unsubstituted diphenyl derivatives, cf. KOELSCH, loc. cit.), on the other hand their cyclization to the pure cis or trans diastereoisomers is original and novel. It is, in effect, very important to have recourse to pure diastereoisomers, since both the qualitative and the quantitative therapeutic activity depends on the cis or trans configuration of the molecule.

The subject of the present invention is hence also the process for the cyclization of the 2,3-diphenyl derivatives of the γ-nitrile-esters which imposes the stereochemistry on the piperidones obtained, in which process—if it is desired to obtain a pure cis derivative the starting material is a pure erythro product and in which process this product is hydrogenated at a pressure of between 10 and 80 bars and at a temperature of between 30° and 100° C., or if it is desired to obtain a pure trans derivative, the starting material is either a pure threo derivative or an erythro derivative which is hydrogenated at a pressure of between 80 and 180 bars and at a temperature of between 80° and 180° C.

The Applicant has been able to demonstrate that this entire family according to the invention possesses different therapeutic actions such as, for example, a vasodilatory action for the γ-nitrile-esters or a psychostimulatory and antidepressant effect in the case of piperidones.

The present invention hence relates to the new drugs according to the invention, and also to the means employed for preparing them and their use.

The invention will be more clearly understood with the aid of further description which follows, which deals with examples of preparation of products according to the invention and also with a report of experiments relating to the pharmacological activity of products according to the invention.

The products of the formulae A and B are prepared by methods similar to those described in the literature.

It should nevertheless be clearly understood that these examples and reports are given solely by way of illustration of the subject of the invention, and in no way constitute a limitation thereof.

A—Examples of preparation of γ-nitrile-esters of the 2,3-diphenyl type and derivatives Example 1

Preparation of ethyl erythro-4-cyano-3-(4-methoxyphenyl)-2-phenylbutanoate -1

20 g (0.125 mol) of para-methoxycinnamonitrile dissolved in 40 cm$^3$ of anhydrous ether are placed with stirring in an atmosphere of nitrogen with 5.8 g (0.148 mol) of sodamide in a 250-cm$^3$ round-bottomed flask maintained at −10° C. by means of an ice/salt bath.

21.4 g (0.130 mol) of ethyl phenylacetate dissolved in 40 cm$^3$ of anhydrous ether are added in the course of 25 min. The temperature is allowed to rise to 10° C. in the course of 1 hour 15 min. The medium then thickens rapidly and solidifies. It is left overnight in the refrigerator.

The mixture is hydrolyzed at −5° to −10° C. (ice/salt) with 10 cm$^3$ of water and 75 cm$^3$ of 4N HCl. It is necessary to add methylene chloride (80 cm$^3$) to make the medium more homogeneous and thereby enable the pH to be adjusted to 7.

The product formed is dissolved completely by adding 100 cm$^3$ of methylene chloride, the mixture is decanted and the organic phase separated. The aqueous phase is extracted with methylene chloride (20 cm$^3$×2). The organic phases are combined and dried over anhydrous sodium sulfate.

After evaporation, 39.7 g (97%) of a solid residue containing only the erythro racemate are obtained. After recrystallization in absolute ethanol (180 cm$^3$), 35.8 g (88%) of a white product are obtained, corresponding to the pure.erythro racemate M.p. 125.5°–126.5° C.

Analysis: C$_{20}$ H$_{21}$ NO$_3$:

|  | C | H | N | O |
|---|---|---|---|---|
| Calc. | 74.46 | 6.57 | 4.41 | 14.75 |
| Fnd. | 74.28 | 6.54 | 4.33 | 14.84 |

IR (KBr): νC≡N, at 2,240 cm$^{-1}$, weak. νC=O, at 1,720 cm$^{-1}$, strong.

Mass spectrometry: (70 eV), m/z (relative intensity) 323 (12,M$^+$), 210 (10), 167 (5), 165 (9), 164 (13), 161 (22), 60 (100) , 152 (5), 145 (9), 118 (5), 117 (4), 105 (6), 91 (5) 89 (4), 77 (5) .

NMR 80 MHz: C$_6$ D$_6$: signals at δ: 7.50–7.00 ppm (7 H, Ar, complex) 7.75 ppm (2 H, Ar, d, J$_{meta\ H\text{-}ortho\ H}$=9 Hz) 4.02 ppm (1 H2, d, J$_{H2\text{-}H3}$=12 Hz) 3.80–3.20 ppm (6 H, complex, including methoxy at 3.30 ppm) 1.72 ppm (2 H4, J$_{H3\text{-}H4}$=5 Hz) 0.57 ppm (3 H,t). CDCl$_3$: signals at δ: 7.60–7.20 ppm (7 H, Ar, complex) 6.87 ppm (2 H, Ar, d, J$_{ortho\ H\text{-}meta\ H}$=10 Hz) 4.10–3.30 ppm (7 H, complex, including methoxy at 3.80 ppm) 2.30 ppm (2 H4, m) 0.92 ppm (3 H, t).

EXAMPLE 2

Preparation of ethyl erythro-4-cyano-2-(4-chlorophenyl)-3-phenylbutanoate -2

6.5 g (0.050 mol) of cinnamonitrile dissolved in 10 cm$^3$ of anhydrous ether are placed with stirring in an atmosphere of nitrogen with 2.55 g (0.065 mol) of sodamide in a 100-cm$^3$ reactor maintained at −5° C. by means of an ice/salt bath.

12 g (0.060 mol) of ethyl para-chlorophenylacetate dissolved in 10 cm$^3$ of anhydrous ether are added in the course of 15 min.

The reaction is continued at −5° C. for 45 min and then at +5° C. for 30 min.

After treatment according to Example 1, 2 is obtained in 69% yield. M.p. 97°–98° C.

Analysis: C$_{19}$ H$_{18}$ Cl NO$_2$:

|  | C | H | Cl | N |
|---|---|---|---|---|
| Calc. | 69.62 | 5.52 | 10.81 | 4.27 |
| Fnd. | 69.47 | 5.45 | 11.07 | 4.29 |
|  |  |  | 11.19 |  |

EXAMPLE 3

Preparation of ethyl threo-4-cyano-2-(4-chlorophenyl)-3-phenylbutanoate 3

10 g (0.030 mol) of 2 are dissolved in 100 cm$^3$ of 0.1N ethanolic potassium hydroxide solution. The medium, brought to reflux for 5 min, is neutralized at +15° C. with 1N HCl. The residue obtained after evaporation is solubilized in 100 cm$^3$ of dichloromethane; the organic phase is washed with water (20 cm$^3$×2), and then dried over anhydrous sodium sulfate. A mixture containing 35% of 3 and 65% of 2 is obtained quantitatively.

The product 3 is isolated by flash chromatography: Silica gel 60, 230–400 mesh-h=25 cm, p$_{N2}$=0.2 bar, elution solvent:hexane/ethyl acetate (90:10). M.p. 104° C. (absolute ethanol). Yield: 30%.

EXAMPLE 4

Preparation of ethyl erythro-4-cyano-3-(4-chlorophenyl)-2-phenylbutanoate 4

39 g (0.238 mol) of 4-chlorocinnamonitrile, melted and then solubilized in 60 cm$^3$ of anhydrous ether, are placed with stirring in an atmosphere of nitrogen with 11 g (0.282 mol) of sodamide in a 500-cm$^3$ round-bottomed flask maintained at −5° C. by means of an ice/salt bath.

43 g (0.261 mol) of ethyl phenylacetate dissolved in 100 cm$^3$ of anhydrous ether are added in the course of 35 min. The reaction medium is then left for 45 min at room temperature before being treated according to Example 1—Yield: 80%. M.p. 124° C.

Analysis: C$_{19}$ H$_{18}$ Cl NO$_2$:

|  | C | H | N | Cl |
|---|---|---|---|---|
| Calc. | 69.62 | 5.52 | 4.27 | 10.81 |

| | C | H | N | Cl |
|---|---|---|---|---|
| Fnd. | 69.61 | 5.49 | 4.27 | 11.08 |
| | | | | 11.18 |

| | C | H | N | O |
|---|---|---|---|---|
| Calc. | 71.37 | 6.55 | 3.96 | 18.10 |
| Fnd. | 71.32 | 6.53 | 4.09 | 18.06 |

EXAMPLE 5

Preparation of ethyl erythro-4-cyano-3-(3,4-dichlorophenyl)-2-phenyl-butanoate 5

11.2 g (0.056 mol) of 3,4-dichlorocinnamonitrile, dissolved in a mixture of methylenechloride (15 cm$^3$) and anhydrous ether (50 cm$^3$) are placed with stirring in an atmosphere of nitrogen with 2.7 g (0.069 mol) of sodamide in a 250- cm$^3$ round-bottomed flask maintained at −8° C. by means of an ice/salt bath.

10.3 g (0.062 mol) of ethyl phenylacetate dissolved in 10 cm$^3$ of anhydrous ether are added in the course of 15 min. The reaction is continued at −8° C. for 1 hour, before the temperature is allowed to rise to +5° C.

After treatment according to Example 1, 5 is obtained in 65% yield. M.p. 117.5°–118° C.

Analysis: $C_{19}H_{17}Cl_2NO_2$:

| | C | H | O | N | Cl |
|---|---|---|---|---|---|
| Calc. | 62.99 | 4.72 | 8.83 | 3.86 | 19.57 |
| Fnd. | 62.78 | 4.79 | 8.55 | 3.85 | 19.35 |

EXAMPLE 6

Preparation of ethyl erythro-4-cyano-3-(4-methylphenyl)-2-phenylbutanoate 6

22 g (0.153 mol) of molten 4-methylcinnamonitrile, 20 cm$^3$ of anhydrous ether and 7 g (0.179 mol) of sodamide are placed with stirring, in an atmosphere of nitrogen, in a 250-cm$^3$ reactor maintained at 12°–13° C.

27 g (0.164 mol) of ethyl phenylacetate are allowed to run into the mixture in the course of 45 min.

After treatment according to Example 1, 6 is obtained in 77% yield. M.p. 120°–120.5° C. (absolute ethanol/ether, 60:40).

Analysis: $C_{20}H_{21}NO_2$:

| | C | H | N | O |
|---|---|---|---|---|
| Calc. | 78.15 | 6.87 | 4.55 | 10.41 |
| Fnd. | 78.17 | 6.95 | 4.76 | 10.37 |

EXAMPLE 7

Preparation of ethyl erythro-4-cyano-2-(3,4-dimethoxyphenyl)-3-phenyl-butanoate 7

To a mixture of 6 g (0.026 mol) of ethyl 3,4-dimethoxyphenylacetate, dissolved in 30 cm$^3$ of anhydrous ether, and 1.1 g (0.028 mol) of sodamide, stirred in an atmosphere of nitrogen and with the ether refluxing, 3.45 g (0.026 mol) of cinnamonitrile dissolved in 10 cm$^3$ of anhydrous ether are added in the course of 20 min.

Refluxing is maintained for 7 hours. By treatment of the reaction medium according to Example 1, 7 may be obtained in 69% yield. M.p. 144° C.

Analysis: $C_{21}H_{23}NO_4$:

EXAMPLE 8

Preparation of ethyl erythro-4-cyano-3-(4-trifluoromethylphenyl)-2-phenyl-butanoate 8

20 g (0.101 mol) of 4-trifluoromethylcinnamonitrile dissolved in 100 cm$^3$ of anhydrous ether are placed with stirring in an atmosphere of nitrogen with 5 g (0.128 mol) of sodamide in a 250-cm$^3$ round-bottomed flask maintained at −5° C. by means of an ice/salt bath.

18.4 g (0.112 mol) of ethyl phenylacetate dissolved in 30 cm$^3$ of anhydrous ether are added in the course of 40 min. The temperature is allowed to rise to +5° C.; the mixture is stirred for 3 h at this temperature. By treatment of the reaction medium according to Example 1, 8 may be obtained in a 69% yield. M.p. 141.5–142.5° C.

Analysis: $C_{20}H_{18}F_3NO_2$:

| | C | H | F | N | O |
|---|---|---|---|---|---|
| Calc. | 66.48 | 5.01 | 15.77 | 3.87 | 8.85 |
| Fnd. | 66.21 | 5.07 | 15.70 | 3.87 | 9.15 |
| | | 4.97 | 15.76 | 3.80 | (by diff.) |

EXAMPLE 9

Preparation of 4-cyano-2-(4-chlorophenyl)-3-phenylbutanoic acid 9

To 10 g (0.030 mol) of 2 or 3 dissolved in 100 cm$^3$ of pyridine, 40 cm$^3$ (0.040 mol) of normal aqueous sodium hydroxide are added at room temperature.

After 24 hours' stirring, the viscous, partially crystallized reaction medium is poured onto ice, acidified with concentrated HCl and then extracted with ether. The combined ether phases are washed with water to neutrality.

The nitrile-acid is obtained quantitatively in the form of a mixture of the racemates in the proportion 62:38.

Recrystallization in a benzene-heptane (50:50) mixture.

Yld=77%.

M.p. 155–165° C.

Corresponding sodium salts

The treatment of the mixture of the above γ-nitrile-acids with sodium hydroxide leads to a mixture of the sodium salts.

M.p. 260°–270° C.

B—Examples of preparation of γ-nitrile-esters of the 3,4-diphenyl type

EXAMPLE 10

Preparation of ethyl erythro-4-cyano-4-(3,4-dimethoxyphenyl)-3-phenyl-butanoate 10

17.62 g (0.100 mol) of ethylcinnamate and 17.72 g (0.100 mol) of 3,4-dimethoxyphenylacetonitrile are placed with stirring in a 250-cm$^3$ round-bottomed flask maintained at 60° C. by means of a thermostatic bath.

2.5 g (0.036 mol) of sodium ethanolate dissolved in 10 cm³ of absolute ethanol are added in the course of 10 min. Stirring is prolonged for 1 hour at 60° C. The mixture is hydrolyzed at −5° C. with water and then dilute HCl. It is necessary to add methylene chloride to make the medium more homogeneous and thereby enable the pH to be adjusted to a value of 7.

The organic phase is washed with water and then dried over anhydrous sodium sulfate.

35 g (99%) of a viscous oil containing a mixture of the erythro and threo racemates in the ratio 75:25 are obtained. The predominant erythro isomer is isolated by flash chromatography using a hexane/ethylacetate (75:25) mixture as eluant (Silica gel 60, 230–400 mesh).

21.2g (60%) of a colorless oil are obtained, which oil crystallizes in anhydrous ether and corresponds to the pure erythro racemate. M.p. 69°–70° C.

Analysis: $C_{21}H_{23}NO_4$:

|       | C     | H    | N    | O     |
|-------|-------|------|------|-------|
| Calc. | 71.36 | 6.55 | 3.96 | 18.11 |
| Fnd.  | 71.26 | 6.48 | 4.09 | 18.20 |

Mass spectrometry: (70 eV); m/z (relative intensity) 353 (41.M+), 308 (11), 265 (8), 178 (16), 177 (100), 176 (43), 162 (8), 136 (8), 135(76), 131 (16), 107 (11), 105 (27).

NRM 80 MHz: CDCl₃, signals at δ: 7.40–7.00 ppm (5 H, Ar, complex) 4.27 ppm (1 H4, d, $J_{H3-H4}$=6.3 Hz) 4.10 ppm (2 H, q) 3.85 ppm (3 H, s, methoxy) 3.70 ppm (3 H, s, methoxy) 3.60–3.40 ppm (1 H3, complex) 3.20–2.55 ppm (2 H2, complex) 1.17 ppm (3 H, t).

EXAMPLE 11

Preparation of ethyl threo-4-cyano-3-(4-chlorophenyl)-4-phenylbutanoate 11

11.7 g (0.100 mol) of benzyl cyanide and 21 g (0.100 mol) of ethyl para-chlorocinnamate, mixed at 0° C., are added in the course of 1/2 h to 200 cm³ of anhydrous ether containing an ethanolic solution of sodium ethanolate (corresponding to 2.3 g of sodium).

The reaction mixture is maintained at 0° C. for 5 hours and then hydrolyzed with dilute HCl. The mixture is decanted and the aqueous phase is extracted with ether; the organic phases are combined and washed to neutrality. The mixture of the two racemates is obtained in an 85% yield.

The pure threo racemate is isolated after two recrystallizations in absolute ethanol. M.p. 108–109° C.

Analysis: $C_{19}H_{18}ClO_2N$:

|       | C     | H    | Cl    |
|-------|-------|------|-------|
| Calc. | 69.61 | 5.53 | 10.88 |
| Fnd.  | 69.40 | 5.42 | 11.06 |

C—Examples of preparation of cyclization products: 3,4-diphenylpiperidones

EXAMPLE 12

Preparation of cis4-(4-methoxyphenyl)-3-phenyl-2-piperidone 12

5 g (0.015 mol) of ethyl 4-cyano-3-(4-methoxyphenyl)-2-phenylbutanoate -1 and 1 g of platinum on charcoal (5% platinum) are placed in an autoclave with 80 cm³ of glacial acetic acid. The medium is brought to 100° C. under a hydrogen pressure of 80 bars for 1 hour 30 min. After the catalyst has been filtered off, the acetic acid evaporated off and the viscous residue obtained taken up with 130 cm³ of methylene chloride, the organic phase is neutralized with saturated sodium bicarbonate solution, washed with distilled water and dried over anhydrous sodium sulfate.

The product obtained after evaporation is solubilized in xylene (70 cm³) and brought to reflux for 4 hours. The piperidone formed precipitates in the cold in this solvent. It is filtered off and washed with anhydrous ether.

2.75 g (63%) of a white crystallized product are obtained, corresponding to the cis racemate 12.

M.p. 187°–188° C.

Analysis: $C_{18}H_{19}NO_2$:

|       | C     | H    | N    | O     |
|-------|-------|------|------|-------|
| Calc. | 76.84 | 6.80 | 4.97 | 11.37 |
| Fnd.  | 76.89 | 6.84 | 4.93 | 11.34 |
|       |       | 6.83 |      |       |

I.R.: (KBr) νC=O, at 1,660 cm⁻¹, strong. νN—H, at 3,180 cm⁻¹, moderate.

Mass spectrometry: (70 eV); m/z (relative intensity) 281 (71.M+.) 147 (100), 134 (59), 118 (73), 91 (16), 90 (19).

NMR 80 MHz: $C_6D_6$: signals at δ: 8.35 ppm (1 H,s, N—H) 7.35–6.80 ppm (5 H, Ar, complex) 6.75–6.35 ppm (4 H, Ar, complex) 3.95 ppm (H3, d, $J_{H3-H4}$=4.8 Hz) 3.25 ppm (3 H, singlet, methoxy) 3.15–2.70 ppm (3 H, complex) 2.20–1.60 ppm (2 H, broad complex),

EXAMPLE 13

Preparation of trans-4-(4-methoxyphenyl)-3-phenyl-2-piperidone 13

5 g (0.015 mol) of ethyl erythro-4-cyano-3-(4-methoxyphenyl)-2-phenylbutanoate -1 and 1 g of platinum on charcoal (5% platinum) are placed in a hydrogenation bomb with 50 cm³ of glacial acetic acid. The medium is brought to 100° C. under an atmosphere of nitrogen (low pressure). Hydrogen is then introduced under high pressure (150 bars) and the temperature is stabilized at 120° C. After one hour's reaction, the mixture is cooled, the catalyst is filtered off and the acetic acid is evaporated off.

The oil obtained, taken up with xylene, is brought to reflux for 4 hours. The xylene is evaporated off and the residue taken up with methylene chloride, and the medium is neutralized by washing with saturated sodium bicarbonate solution and then with distilled water.

After drying of the organic phase over sodium sulfate, filtration and evaporation of the solvent, 4.35 g (100%) of a viscous residue is obtained which is precipitated by adding anhydrous ether.

After recrystallization in an absolute ethanol/ether (70:30) mixture, 3.2 g (73%) of a crystallized product are obtained, corresponding to the pure trans racemate 13. M.p. 144°–146° C.

Analysis: $C_{18}H_{19}NO_2$:

|       | C     | H    | N    | O     |
|-------|-------|------|------|-------|
| Calc. | 76.84 | 6.80 | 4.97 | 11.37 |
| Fnd.  | 76.64 | 6.91 | 4.46 | 11.50 |

-continued

| | C | H | N | O |
|---|---|---|---|---|
| | 76.78 | 7.16 | 4.61 | 11.61 |

I.R.: (KBr) $\nu$C=O, at 1,655 cm$^{-1}$, strong. $\nu$N—H, at 3,170 cm$^{-1}$, moderate.

Mass spectrometry: (70 eV); m/z (relative intensity) 281 (60:M+.), 147 (100), 134 (66), 118 (71), 91 (34).

NMR: 80 MHz: $C_6 D_6$: signals at δ: 8.45 ppm (1 H, s, N—H) 7.05 ppm (5 H, Ar, complex) 6.65 ppm (4 H, Ar, complex) 3.60 ppm (1 H3, d, $J_{H3-H4}$=10 Hz) 3.20 ppm (3 H, s, methoxy) 3.05-2.65 ppm (3 H, complex) 1.70-1.35 ppm (2 H, complex).

EXAMPLE 14

Preparation of cis-3-(4-chlorophenyl)-4-phenyl-2-piperidone 14

13.5 g (0.041 mol) of 2 and 2 g of platinum on charcoal (5% platinum) are placed in an autoclave with 70 cm³ of glacial acetic acid. The mixture is brought to °C. under a pressure of 10 bars for 4 hours.

After treatment according to Example 12, 14 is obtained in a 51% yield. M.p. 180°-181° C. (xylene).

Analysis: $C_{17} H_{16}$ Cl NO:

| | C | H | Cl | N |
|---|---|---|---|---|
| Calc. | 71.45 | 5.63 | 12.40 | 4.90 |
| Fnd. | 71.42 | 5.57 | 12.64 | 4.70 |

EXAMPLE 15

Preparation of trans-3-(4-chlorophenyl)-4-phenyl-2-piperidone 15

1st route: 6.6 g (0.020 mol) of 2 and 0.8 g of platinum on charcoal (5% platinum) are placed in an autoclave with 65 cm³ of glacial acetic acid. The medium is brought to 90° C. under a low pressure of nitrogen, hydrogen only being introduced under high pressure (130 bars) after stabilization of the temperature at 90° C. After 1 hour's reaction, the mixture is treated according to Example C1.

However, the crude product obtained is composed of 90% of the trans racemate 15 and 10% of the cis racemate 14.

15 is separated by H.P.L.C. on a Partisil 10 semi-preparative column, using an ethyl acetate/methanol (97:3) mixture as elution solvent. Yield: 72%.

M.p. 139°-141° C.

Analysis: $C_{17} H_{16}$ Cl NO:

| | C | H | Cl | N |
|---|---|---|---|---|
| Calc. | 71.45 | 5.63 | 12.40 | 4.90 |
| Fnd. | 71.44 | 5.34 | 12.51 | 4.93 |
| | | | 12.48 | |

2nd route: 2.6 g (7.9×10$^{-3}$ mol) of 3 and 0.3 g of platinum on charcoal (5% platinum) are treated according to Example 14, to give 15 in a 65% yield.

EXAMPLE 16

Preparation of cis-4-(4-chlorophenyl)-3-phenyl-2-piperidone 16

10 g (0.030 mol) of 4 and 2 g of platinum on charcoal (5% platinum) are placed in a autoclave with 150 cm³ of glacial acetic acid. The medium is brought to 80° C. under a pressure of 40 bars for 5 hours.

After filtration, neutralization and recrystallization in an anhydrous ether/hexane/methylene chloride (60:20:20) ternary mixture, 16 is obtained in a 77% yield.

M.p. 168° C.

Analysis: $C_{17} H_{16}$ Cl NO:

| | C | H | N | O | Cl |
|---|---|---|---|---|---|
| Calc. | 71.45 | 5.63 | 4.90 | 5.59 | 12.40 |
| Fnd. | 71.25 | 5.57 | 4.86 | 5.70 | 11.83 |
| | 71.47 | 5.58 | 5.00 | 5.54 | 12.07 |

EXAMPLE 17

Preparation of trans-4-(4-chlorophenyl)-3-phenyl-2-piperidone 17

10 g (0.030 mol) of 4 and 2 g of platinum on charcoal (5% platinum) are placed in an autoclave with 80 cm³ of glacial acetic acid. The medium is brought to 180° C. under a low pressure of nitrogen, hydrogen only being introduced under high pressure (180 atm) when the temperature has stabilized. After 30 min of stirring, a mixture of trans 17 and cis 16 racemates is obtained in the ratio 90:10.

After separation according to Example 15 (1st route) and recrystallization in acetone, 17 is obtained in a 50% yield.

M.p. 156°-157° C.

Analysis: $C_{17} H_{16}$ NClO:

| | C | H | N | Cl |
|---|---|---|---|---|
| Calc. | 71.45 | 5.63 | 4.90 | 12.40 |
| Fnd. | 71.21 | 5.46 | 4.72 | 12.33 |
| | | | | 12.42 |

EXAMPLE 18

Preparation of cis-4-(3,4-dichlorophenyl)-3-phenyl-2-piperidone 18

The treatment of 5 according to the conditions of Example 16, followed by refluxing in xylene for 2 hours 30 min and recrystallization in acetone, leads to 18 in a 50% yield. M.p. 169° C.

Analysis: $C_{17} H_{15}$ NO $C_2$:

| | C | H | N |
|---|---|---|---|
| Calc. | 63.76 | 4.72 | 4.37 |
| Fnd. | 62.80 | 4.72 | 4.54 |
| | 63.83 | 4.94 | 4.35 |

EXAMPLE 19

Preparation of trans-4-(3,4-dichlorophenyl)-3-phenyl-2-piperidone 19

10 g (0.027 mol) of 5 and 2 g of platinum on charcoal (5% platinum) are placed in an autoclave with 60 cm³ of glacial acetic acid. The medium is brought to 150° C. under a low pressure of nitrogen, hydrogen only be introduced under high pressure (175 bars) when the temperature has stabilized. After 1 hour 15 min of reaction, a mixture of the trans and cis racemates is obtained in the ratio 93:7.

After separation according to Example 15 (1st route) and recrystallization in acetone, 19 is obtained in a 48% yield. M.p. 154°–155° C.

Analysis: $C_{17} H_{15} NCl_2 O$:

|       | C     | H    | N    | Cl    |
|-------|-------|------|------|-------|
| Calc. | 63.76 | 4.72 | 4.37 | 22.14 |
| Fnd.  | 63.54 | 4.67 | 4.30 | 22.04 |
|       | 63.61 | 4.71 | 4.31 |       |

EXAMPLE 20

Preparation of cis-4-(4-methylphenyl)-3-phenyl-2-piperidone 20

20 g (0.065 mol) of 6 and 130 cm³ of glacial acetic acid are stirred for 6 hours at 90° C. under a hydrogen pressure of 40 bars in the presence of Raney nickel. After treatment and recrystallization in an absolute ethanol-ether mixture, 20 is obtained in an 87% yield. M.p. 174° C.

Analysis: $C_{18} H_{19} NO$:

|       | C     | H    | N    | O    |
|-------|-------|------|------|------|
| Calc. | 81.48 | 7.21 | 5.27 | 6.02 |
| Fnd.  | 80.59 | 7.26 | 5.05 | 7.11 |
|       | 80.84 | 7.15 | 4.95 | 7.06 |

Calculated with 1/5 of a mol of water per mol of piperidone:

| 80.40 | 7.22 | 5.21 | 7.14 |
|-------|------|------|------|

EXAMPLE 21

Preparation of trans-4-(4-methylphenyl)-3-phenyl-2-piperidone 21

10 g (0.032 mol) of 6 and 60 cm³ of glacial acetic acid are stirred for 4 hours at 150° C. under a hydrogen pressure of 100 bars.

After treatment and recrystallization in an absolute ethanol/anhydrous ether (60:40) mixture, 21 is obtained in a 55% yield. M.p. 176° C.

Analysis: $C_{18} H_{19} NO$:

|       | C     | H    | N    | O    |
|-------|-------|------|------|------|
| Calc. | 81.48 | 7.21 | 5.27 | 6.02 |
| Fnd.  | 81.50 | 7.24 | 4.81 | 6.22 |
|       | 81.79 | 7.32 | 4.84 | 6.15 |

EXAMPLE 22

Preparation of cis-3-(3,4-dimethoxyphenyl)-4-phenyl-2-piperidone 22

5 g (0.014 mol) of 7 and 1 g of platinum on charcoal (5% platinum) are placed in an autoclave with 80 cm³ of glacial acetic acid. The medium is brought to 60° C. under a hydrogen pressure of 30 bars for 5 hours.

After treatment according to Example C1 followed by recrystallization in absolute ethanol, 22 is obtained in a 70% yield. M.p. 195°–197° C.

Analysis: $C_{19} H_{21} NO_3$:

|       | C     | H    | N    | O     |
|-------|-------|------|------|-------|
| Calc. | 73.29 | 6.79 | 4.49 | 15.41 |
| Fnd.  | 73.26 | 6.67 | 4.65 | 15.42 |

EXAMPLE 23

Preparation of trans-3-(3,4-dimethoxyphenyl)-4-phenyl-2-piperidone 23

5 g (0.014 mol) of 7 and 1 g of platinum on charcoal (5% platinum) are placed in an autoclave with 60 cm³ of glacial acetic acid. The medium is brought to 80° C. under a hydrogen pressure of 80 bars for 3 hours.

After treatment according to Example 12 followed by recrystallization in an absolute ethanol/ether (60:40) mixture, 23 is obtained in a 78% yield. M.p. 154° C.

Analysis: $C_{19} H_{21} NO_3$:

|       | C     | H    | N    | O     |
|-------|-------|------|------|-------|
| Calc. | 73.29 | 6.79 | 4.49 | 15.41 |
| Fnd.  | 73.30 | 6.77 | 4.28 | 15.65 |

EXAMPLE 24

Preparation of cis-4-(4-trifluoromethylphenyl)-3-phenyl-2-piperidone 24

7 g (0.019 mol) of 8 and 1.5 g of platinum on charcoal (5% platinum) are placed in an autoclave with 75 cm³ of glacial acetic acid. The medium is brought to 40° C. under a hydrogen pressure of 5 bars for 7 hours. After treatment according to Example C1 and recrystallization in an anhydrous ether/hexane mixture, 24 is obtained in a 77% yield. M.p. 155°–156° C.

Analysis: $C_{18} H_{16} F_3 NO$:

|       | C     | H    | F     | N    | O              |
|-------|-------|------|-------|------|----------------|
| Calc. | 67.70 | 5.04 | 17.84 | 4.38 | 5.01           |
| Fnd.  | 67.70 | 5.19 | 17.82 | 4.23 | 5.06 (by diff.) |

EXAMPLE 25

Preparation of cis-3-(3,4-dihydroxyphenyl)-4-phenyl-2-piperidone 25

To a solution of 4 g (0.013 mol) of 22 in 150 cm³ of anhydrous methylene chloride, stirred under an atmosphere of nitrogen at −60° C., a solution of 10 g (0.040 mol; 3.8 cm³) of boron tribromide in 140 cm³ of anhydrous methylene chloride is added dropwise in the course of 2 hours 30 min. The temperature is maintained at −60° C. for 1 hour. The stirring is continued at room temperature for 4 hours 30 min.

The mixture is cooled again to −60° C. and 100 cm³ of anhydrous methanol are added dropwise, and the temperature is then allowed to rise while the reaction medium is subjected to a strong stream of nitrogen in order to expel the excess hydrobromic acid formed. After one hour's stirring at room temperature, the solution is concentrated under vacuum (θ<30° C.), and the oil obtained is solubilized in 100 cm³ of methylene chloride. The dihydroxylated piperidone is precipitated by adding 100 cm³ of water with stirring. The precipitate is filtered on sintered glass; it is washed with methylene chloride, with sodium bicarbonate solution and then with water to neutrality. 25 is obtained in an 80% yield.

M.p. 253°–255° C.

Analysis: $C_{17} H_{17} NO_3$:

|  | C | H | N | O |
|---|---|---|---|---|
| Calc. | 72.07 | 6.04 | 4.94 | 16.94 |
| Fnd. | 71.66 | 6.00 | 4.96 | 17.38 |
|  | 71.64 | 6.23 | 4.86 | 17.27 |

Calculated with 0.1 mol of water per mol of piperidone

| 71.61 | 6.07 | 4.91 | 17.39 |
|---|---|---|---|

EXAMPLE 26

Preparation of trans-3-(3,4-dihydroxyphenyl)-4-phenyl-2-piperidone 26

The treatment of 23 under the conditions of Example C14 lead to 26 in an 84% yield. M.p. 235°–237° C.

Analysis: $C_{17} H_{17} NO_3$:

|  | C | H | N | O |
|---|---|---|---|---|
| Calc. | 72.07 | 6.04 | 4.94 | 16.94 |
| Fnd. | 71.94 | 5.98 | 4.94 | 17.14 |

EXAMPLE 27

Preparation of trans-4-(4-hydroxyphenyl)-3-phenyl-2-piperidone 27

The treatment of 13 under the conditions of Example 25 followed by recrystallization in absolute ethanol leads to 27 in a 71% yield.

M.p. 233°–234° C.

Analysis: $C_{17} H_{17} NO_2$:

|  | C | H | N |
|---|---|---|---|
| Calc. | 76.38 | 6.41 | 5.24 |
| Fnd. | 76.46 | 6.21 | 5.17 |

EXAMPLE 28

Preparation of trans-4-(4-benzyloxyphenyl)-3-phenyl-2-piperidone 28

1.34 g (0.005 mol) of 27, dissolved in a mixture of dry benzene (17 cm³) and D.M.S.O. (1 cm³) are added under an atmosphere of nitrogen to sodium hydride (0.3 g of 50% strength NaH in oil, washed several times with benzene).

The heterogeneous mixture is stirred and heated under reflux for 1 hour and then cooled, and a solution of 1.07 g (6.25×10⁻³ mol) of benzyl bromide in benzene is then added. After 1 hour's heating under reflux, the mixture, which has become clear, is stirred again overnight at room temperature.

10 cm³ of water are added and the mixture is extracted with methylene chloride. After the product is washed with anhydrous ether and then recrystallized in methanol, 28 is obtained in a 78% yield. M.p. 196° C.

Analysis: $C_{24} H_{23} NO_2$:

|  | C | H | N |
|---|---|---|---|
| Calc. | 80.64 | 6.48 | 3.92 |
| Fnd. | 79.73 | 6.25 | 3.85 |
|  | 79.56 |  |  |

Calculated with 0.22 mol of water per mol of piperidone

| 79.76 | 6.53 | 3.87 |
|---|---|---|

EXAMPLE 29

Preparation of trans-4-(4-mesyloxyphenyl)-3-phenyl-2-piperidone 29

To a solution of 1.34 g (0.005 mol) of 27 in 10 cm³ of anhydrous pyridine, 1.14 g (0.01 mol; 0.77 cm³) of methanesulfonyl chloride are added under an atmosphere of nitrogen at 0° C. The mixture is stirred for 1 hour at between 0° and 3° C. before being poured into 70 cm³ of cold water. This mixture is extracted with methylene chloride and washed to neutrality. After evaporation and recrystallization in methanol, 29 is obtained in 61% yield. M.p. 199° C.

Analysis: $C_{18} H_{19} NO_4 S$:

|  | C | H | N |
|---|---|---|---|
| Calc. | 62.59 | 5.55 | 4.05 |
| Fnd. | 62.47 | 5.62 | 4.03 |

EXAMPLE 30

Preparation of ethyl 4-cyano-3-(4-chloro-3-trifluoromethylphenyl)-2-phenylbutanoate in the form of a mixture of the erythro and threo racemates 30

15 g (0.091 mol) of ethyl phenylacetate, diluted in 150 cm³ of anhydrous ether, are placed with stirring in an atmosphere of nitrogen with 4.3 g (0.110 mol) of sodamide in a 500-cm³ round-bottomed flask maintained at between −12° C. and −15° C. by means of an ice/salt bath.

20 g (0.086 mol) of 4-chloro-3-trifluoromethylcinnamonitrile dissolved in 80 cm³ of anhydrous THF are added in the course of 45 min at a temperature of between −12° C. and −15° C. The temperature is allowed to rise to −5° C. and the mixture is stirred for 1 hour 10 min before being hydrolyzed at between −5° C. and −10° C. with 50 cm³ of water and then 6N hydrochloric acid (approximately 40 cm³) to neutrality.

The mixture is evaporated to dryness to recover quantitatively a beige amorphous compound predominantly containing the erythro racemate (erythro/threo ≈ 70:30; assay by analytical GC on an Apiezon M column at 200° C., add NMR 80 MHz, CDCL₃, on triplets).

After recrystallization in a hexane/absolute ethanol (70:30) mixture, 26.2 g of a powder is obtained still containing the mixture of the erythro and threo racemates 30 (E/T≈: 73:27). Yld=76%.

Analysis: $C_{20} H_{17} Cl F_3 NO_2$:

|  | C | H | Cl | F | N |
|---|---|---|---|---|---|
| Calc. | 60.69 | 4.32 | 8.95 | 14.40 | 3.53 |
| Fnd. | 60.62 | 4.73 | 8.88 | 14.72 | 3.46 |

IR(KBr): $\nu C\equiv N$ at 2,250 cm$^{-1}$, moderate. $\nu C=O$ at 1,710 cmPHU $-1$, strong.

Mass spectrometry: (70 eV), m/z (relative intensity): 397.9 (0.5); 396.9 (2.6); 395.9 (1.9); 395.0 (8.3); 321.9 (10.7); 281.9 (15.0); 164.0 (50.0); 163.0 (100.0); 135.0 (30.8).

NMR 80 MHz: CDCl$_3$: signals at δ: 7.9–7.0 ppm (8 H, Ar, complex) 4.4–3.5 ppm (4 H, complex)

| 2.9 ppm / 2.4 ppm | 2 H | H4 threo component, d, $J_{H3-H4}$ = 5 Hz / H4 erythro component, narrow complex |
|---|---|---|
| 1.2 ppm / 1.0 ppm | 3 H | t threo component / t erythro component |

Comment: erythro/threo component ratio≃73:27. C$_6$D$_6$: signals at δ: 7.80–6.70 ppm (8 H, Ar, complex). 4.00–3.00 ppm (4 H, complex).

| 2.20 ppm / 1.55 ppm | 2 H | H4, threo component, narrow complex / H4, erythro component d, $J_{H3-H4}$ = 5Hz. |
|---|---|---|
| 0.85 ppm / 0.55 ppm | 3 H | t, threo component / t, erythro component. |

EXAMPLE 31

Preparation of trans-4-(4-trifluoromethylphenyl-3-phenyl-2-piperidone 31

15 g (0.041 mol) of ethyl erythro-4-cyano-3-(4-trifluoromethylphenyl)-2-phenylbutanoate 8 and 3 g of platinum on charcoal (5% platinum) are placed in an autoclave with 120 cm$^3$ of glacial acetic acid. The mixture is brought to 120° C. under an atmosphere of nitrogen (low pressure). Hydrogen is then introduced under high pressure (120 bars) and the mixture is stirred for 3 hours. The mixture is cooled, the catalyst filtered off and the acetic acid evaporated off. The oil obtained, taken up in xylene (300 cm$^3$), is brought to reflux for 3 hours. The xylene is evaporated off and the residue taken up with methylene chloride, and the medium is neutralized by washing with saturated sodium bicarbonate solution and then distilled water. After drying of the organic phase over anhydrous sodium sulfate, filtration, and evaporation of the solvent, a viscous residue is obtained which crystallizes in a little ether. 6.5 g (49%) of white crystals are thereby recovered containing approximately 85% of the trans racemate and 15% of the cis racemate (analytical H.P.L.C. assay, Partisil 10 col- Analysis: C$_{18}$ H$_{16}$ F$_3$ NO:

|  | C | H | N | F |
|---|---|---|---|---|
| Calc. | 67.70 | 5.05 | 4.38 | 17.84 |
| Fnd. | 67.86 | 5.04 | 4.33 | 17.73 |

Mass spectrometry: (70 eV), m/z (relative intensity): 319 (23,M+), 119(6), 118(57), 92(10), 91(100), 90(12).

NMR 60 MHz: C$_6$D$_6$: signals at δ: 8.80 ppm (1 H, N—H, s), 7.30–6.30 ppm (9 H, Ar, complex), 3.35 ppm (1 H3, d, $J_{H3-H4}$ = 10 Hz), 3.00–2.50 ppm (3 H, complex), 1.45–1.10 ppm (2 H, complex).

EXAMPLE 32

Preparation of trans-4-(4-chloro-3-trifluoromethylphenyl)-3-phenyl-2-piperidone 32

26 g (0.065 mol) of the mixture of racemates of ethyl 4-cyano-3-(4-chloro-3-trifluoromethylphenyl)-2-phenylbutanoate 30 (E/T~73:27) and 5 g of platinum on charcoal (5% platinum) are placed in an autoclave with 180 cm$^3$ of glacial acetic acid. The medium is brought to 120° C. under an atmosphere of nitrogen (low pressure). Hydrogen is then introduced under high pressure (120 bars) and the mixture is stirred for 3 hours 30 min.

After the catalyst has been filtered off, the acetic acid evaporated off and the viscous residue obtained taken up with methylene chloride, the organic phase is neutralized with saturated sodium bicarbonate solution, washed with water and dried over anhydrous sodium sulfate.

After evaporation and precipitation in anhydrous ether, a crystallized product is obtained containing a mixture of the cis and trans racemates in the ratio 15:85 (analytical H.P.L.C. assay: Partisil 10 column; ethyl acetate/methanol, 97:3).

Rapid chromatography on A.S.T.M. 230–400 mesh silica, using ethyl acetate as eluant, enables the trans racemate to be separated.

After recrystallization in a hexane/absolute ethanol (80:20) mixture, 14 g (60%) of the pure trans racemate 32 are obtained. M.p. 144°–146° C.

Analysis: C$_{18}$ H$_{15}$ Cl F$_3$ NO:

|  | C | H | Cl | F | N |
|---|---|---|---|---|---|
| Calc. | 61.11 | 4.26 | 10.02 | 16.11 | 3.95 |
| Fnd. | 61.49 | 4.34 | 9.98 | 16.28 | 3.86 |

IR (KBr): C=O at 1,660 cm$^{-1}$, strong. $\nu$N—H at 3,190 cm$^{-1}$, moderate.

Mass spectrometry: (70 eV), m/z (relative intensity): 356.0 (1.2); 355.0 (5.8); 354.0 (3.8); 353.0 (18.4); 351.9 (1.2); 118.0 (64.1); 91.0 (71.8); 28.1 (100.0).

NMR 80 MHz: C$_6$D$_6$: signals at δ: 8.80 ppm (1 H, s, N—H), 7.30–6.30 ppm (8 H, Ar, complex), 3.30 ppm (1 H3, d, $J_{H3-H4}$ = 10 Hz), 3.05–2.40 ppm (3 H, complex), 1.50–1.00 ppm (2 H, complex).

added under nitrogen at 0° C. The mixture is stirred for 2 hours 30 mins at 0° C., and then 48 hours at room temperature. The reaction mixture is then poured onto 50 g of ice. A spatulaful of sodium bicarbonate is added, and the mixture is stirred and then extracted with methylene chloride (3 times 60 cm³).

The organic phase is washed successively with water, dilute hydrochloric acid, and water to neutrality, and is then dried over anhydrous sodium sulfate. After filtration, and evaporation of the solvent, 2.6 g (84%) of a friable white foam are obtained, and this is recrystallized in methanol. After being washed with ether and dried, 1.65 g (53%) of the trans compound 33 is obtained in the form of white crystals, m.p. 201°–204° C.

Analysis: $C_{19}H_{19}NO_3$:

|  | C | H | N |
|---|---|---|---|
| Calc. | 73.76 | 6.19 | 4.52 |
| Fnd. | 73.98 | 6.14 | 4.40 |
|  |  | 6.36 |  |

IR(KBr): $\nu$N—H at 3,340 cm$^{-1}$, weak, $\nu$C=O at 1,740 cm$^{-1}$, strong (ester), $\nu$C=O at 1,650 strong (lactam).

Mass spectrography: (70 eV); m/z (relative intensity): 311.0 (1.1); 310.0 (6.6); 309.0 (16.8,M+); 267.1 (35.9); 176.1 (5.1); 165.1 (6.2); 147.0 (19.1); 133.0 (38.0); 120.0 (25.5); 119.0 (12.6); 118.0 (100); 107.0 (5.0 ); 91.0 (14.4); 89.9 (16.2); 89.0 (6.0).

EXAMPLE 34

Preparation of trans-3-phenyl-4-(4-phenoxyphenyl)-2-piperidone 34

6.2 g (0.023 mol) of trans-4-(4-hydroxyphenyl)-3-phenyl-2-piperidone 27, 8.6 g (0.023 mol) of diphenyliodonium bromide and a solution of 0.94 g of sodium hydroxide in 170 cm³ of double-distilled water are brought to reflux with stirring for 24 hours. The mixture is cooled and extracted with methylene chloride. The organic phase is washed successively with 5% strength sodium hydroxide solution and with water to neutrality, and dried over anhydrous sodium sulfate. After filtration and evaporation, 6 g of a solid are obtained and this is recrystallized in methanol. 5.3 g (66%) of pure 34 are obtained, m.p. 157°–159° C.

Analysis: $C_{23}H_{21}NO_2$:

|  | C | H | N |
|---|---|---|---|
| Calc. | 80.44 | 6.16 | 4.07 |
| Fnd. | 80.43 | 5.90 | 4.04 |

IR(KBr): $\nu$N—H at 3,200 cm$^{-1}$, moderate, $\nu$C=O at 1,660 cm$^{-1}$, strong, $\nu$C—O—C at 1,240 cm$^{-1}$, strong.

Mass spectrometry: (70 eV); m/z (relative intensity): 345.0 (2.4); 344.0 (17.5); 343.0 (63.2;M+); 210.0 (9.3); 209.0 (56.4); 197.0 (10.9); 196.0 (65.1); 178.0 (7.5); 167.0 (5.2); 165.0 (8.8); 152.0 (5.2); 147.0 (19.7); 119.0 (10.7); 118.0 (100.0); 116.0 (20.5); 115.0 (15.6); 91.0 (14.1); 89.9 (19.9); 89.0 (5.7); 77.1 (21.2); 65.1 (5.1).

EXAMPLE 35

Preparation of trans-4-(4-ethoxyphenyl)-3-phenyl-2-piperidone 35

To a solution of 6.7 g (0.025 mol) of trans-4-(4-hydroxyphenyl)-3-phenyl-2-piperidone 35 and 1.3 g of sodium hydroxide pellets in 50 cm³ of water, maintained stirred, 3.6 cm³ (0.027 mol; 4.23 g) of diethyl sulfate are added dropwise at 0° C. After 5 hours' refluxing (92° C.), the mixture is cooled and the suspension thereby obtained is extracted with methylene chloride. The organic phase is washed successively with dilute sodium hydroxide solution, and with water to neutrality, and dried over sodium sulfate. 5.9 g (80%) of a white foam are obtained, and this is recrystallized in an ethanol/ether (70:30) mixture. 5 g (67%) of pure 35 are recovered, m.p. 161°–162° C. (change of appearance at 153° C.).

Analysis: $C_{19}H_{21}NO_2$:

|  | C | H | N |
|---|---|---|---|
| Calc. | 77.26 | 7.16 | 4.74 |
| Fnd. | 77.13 | 7.20 | 4.79 |

Mass spectrography: (70 eV); m/z (relative intensity): 297.1 (1.1); 296.1 (8.5); 295.1 (43.2:M+°); 162.1 (10); 161.0 (79.1); 149.0 (6.3); 148.0 (52.6); 147.0 (13.6); 133.0 (17.4); 120.0 (30.0); 119.0 (14.0); 118.0 (100.0); 115.0 (5.4); 91.0 (14.8); 89.9 (20.1); 89.0 (5.6).

EXAMPLE 36

Preparation of ethyl erythro-4-cyano-3-(4-dimethylaminophenyl)-2-phenylbutanoate 36

1. Preparation of trans-4-dimethylaminocinnamonitrile

To a round-bottomed flask containing 27.65 g 0.200 mol) of potassium carbonate, 35 cm³ of water and 21.25 g (0.119 mol) of diethyl cyanomethylphosphonate, 14.92 g (0.100 mol) of 4-dimethylaminobenzaldehyde, dissolved in the minimum of tetrahydrofuran, are added.

After 5 hours' refluxing (72° C.), the mixture is cooled and 200 cm³ of water are added. The yellow precipitate obtained contains mainly the trans isomer. After recrystallization in 95° strength ethanol, 11 g (64%) of pure trans-4-dimethylaminocinnamonitrile are obtained, m.p. 168°–169° C.

2. To a mixture of 9 g (0.052 mol) of trans-4-dimethylaminocinnamonitrile in 130 cm³ of anhydrous ether and 2.6 g (0.066 mol) of sodamide, a solution of 9.1 g (0.055 mol) of ethyl phenylacetate in 40 cm³ of ether is added in the course of 25 minutes with stirring and at 0° C. As soon as the addition is finished, the mixture is brought to room temperature and stirring is continued for 1 hour before the mixture is left standing overnight. The reaction medium is then hydrolyzed with 5 cm³ of water and 30 cm³ of 4N hydrochloric acid to neutrality, and is then extracted with methylene chloride. The organic phase is washed with water and then dried over anhydrous sodium sulfate. After filtration and evaporation, a brown solid is recovered containing an erythro/threo mixture in the proportion 95:5. On recrystallization in absolute ethanol, 14.1 g (80%) of the pure erythro compound 36 are obtained, m.p. 141° C.

EXAMPLE 37

Preparation of trans-4-(4-dimethylaminophenyl)-2-piperidone 37

11.3 g of the pure erythro compound 36, 2 g of platinum on charcoal (5% Pt/C) and 50 cm³ of glacial acetic acid are placed in a 250—cm³ autoclave. The mixture is heated to 120° C., the temperature rise being accomplished under a low pressure of nitrogen. Hydrogen is only introduced under high pressure (150 bar) when the temperature has stabilized. After the customary treatment, a beige oil is recovered which is solubilized in xylene, the whole mixture is brought to reflux for 4 hours and the xylene is then evaporated off. The residue is dissolved in methylene chloride. The organic phase is neutralized with saturated sodium bicarbonate solution, then washed with water and dried over anhydrous sodium sulfate. After evaporation, 9 g (92%) of a beige solid are obtained containing a trans/cis mixture in the proportion 93:7. Recrystallization of this crude product in ethanol does not enable the pure trans diastereoisomer to be isolated, and this latter is isolated pure by flash chromatography:

ASTM 230–400 mesh silica gel column,
mobile phase: chloroform/ethanol, 99:1.

7 g (71%) of the trans compound 37 are obtained, m.p. 218°–219° C., on recrystallization in absolute ethanol.

Analysis: $C_{19} H_{22} N_2 O$:

|  | C | H | N | O |
|---|---|---|---|---|
| Calc. | 77.51 | 7.53 | 9.51 | 5.43 |
| calc (0.175 mol H$_2$O) | 76.69 | 7.56 | 9.41 | 6.31 |
| Fnd. | 76.68 | 7.39 | 9.15 | 6.39 |

Mass spectrography: (70 eV); m/z (relative intensity): 295.1 (9.6); 294.1 (47.3;$M^{+o}$); 161.0 (11.9); 160.0 (100.0); 148.1 (13.1); 147.1 (39.9); 146.1 (14.1); 118.0 (14.2); 90.0 (5.1).

EXAMPLE 38

Preparation of ethyl erythro-4-cyano-3-(2,4-dichlorophenyl)-2-phenyl-butanoate 38

1. Preparation of trans-2,4-dichlorocinnamonitrile

To a solution of 8 g of potassium carbonate in 10 cm³ of water, 6 g (0.034 mol) of diethyl cyanomethylphosphonate are added followed by 5 g of 2,4-dichlorobenzaldehyde solubilized in 10 cm³ of anhydrous tetrahydrofuran. The mixture is left stirred for 10 minutes at room temperature and 20 cm³ of water are added. The precipitate formed is washed with water to neutrality (8 times with 20 cm³ of water), and then washed with an ether/hexane mixture. 3.7 g (74%) of trans-2,4-dichlorocinnamonitrile are obtained in the form of white crystals, m.p. 156° C.

2. 23 g (0.14 mol) of ethyl phenylacetate dissolved in 250 cm³ of anhydrous ether are placed with stirring and under nitrogen with 6 g (0.153 mol) of sodamide in a 1-liter round-bottomed flask maintained at 0° C. by means of ice, and 25 g (0.126 mol) of trans-2,4-dichlorocinnamonitrile in 350 cm³ of anhydrous tetrahydrofuran are then added in the course of 30 minutes. After 6 hours' stirring at 0° C., the mixture is hydrolyzed with 20 cm³ of water, and then with 6N HCl, until neutrality is obtained. After evaporation, and dissolution of the residue in methylene chloride, the organic phase is washed with water and dried over anhydrous sodium sulfate. The crude product obtained only contains the erythro racemate. It is recrystallized in absolute ethanol to give 32 g (70%) of erythro 38 in the form of white crystals, m.p. 95°–96° C.

Analysis: $C_{19} H_{17} Cl_2 NO_2$:

|  | C | H | Cl | N |
|---|---|---|---|---|
| Calc. | 62.99 | 4.72 | 19.57 | 3.86 |
| Fnd. | 62.93 | 4.86 | 19.85 | 3.76 |

IR (KBr): $\nu C\equiv N$ at 2,200 cm$^{-1}$, moderate, $\nu C=O$ at 1,730 cm$^{-1}$, strong.

Mass spectrometry: (70 eV); m/z (relative intensity): 365.1 (0.9;$M^{+o}$); 364.0 (1.0); 363.0 (4.6;$M^{+o}$); 362.0 (1.6); 361.0 (6.7;$M^{+o}$); 326.1 (6.2); 289.9 (7.6); 288.0 (11.5); 250.0 (8.2); 248.0 (12.4); 213.0 (9.4); 199.9 (14.0); 198.0 (21.6); 179.1 (5.0); 178.1 (28.7); 177.1 (8.0); 176.1 (8.8); 165.0 (12.5); 164.1 (100); 163.0 (91.3); 136(13.8); 135(39.3); 118(7.2); 107(27.8); 106(6.4); 91.0(34.9); 89.9(5.9); 89.0(6.7); 88.0(7.0); 79.0(14.6); 77.1(7.6).

EXAMPLE 39

Preparation of ethyl threo-4-cyano-3-(2,4-dichlorophenyl)-2-phenylbutanoate 39

The epimerization of the erythro isomer 38 in basic medium (0.1M ethanolic potassium hydroxide), followed by separation by flash chromatography (230–400 mesh silica gel, eluant: hexane/ethyl acetate, 90:10) enables the pure threo isomer 39 to be obtained in the form of crystals, m.p. 78°–79° C.

EXAMPLE 40

Preparation of trans-3-(2,4-dichlorophenyl)-4-phenyl-2-piperidone 40 m.p. 170°–171° C. (recrystallized in ethanol).

Reports of the Pharmacological Experiments

I—As regards the piperidones

Studies of the acute toxicity in mice, motor activity in mice, stereotypy in rats, antireserpine activity in mice, antiapomorphine activity in mice, antioxotremorine activity in mice, action on yohimbine toxicity in mice and interaction with sodium barbital and with pentobarbital may be summarized as follows:

1 Effects in some tests:
  Toxicity greater in grouped mice
  Increase in motor activity in mice
  Stereotyped movements in rats
  Antagonism of sodium barbital-induced sleep in mice
  Antagonimm of reserpine-induced hypothermia
  Antagonism of hypothermia induced by apomorphine (high dose)
  Antagonism of oxotremorine-induced hypothermia
  Slight potentiation of yohimbine toxicity.

2. Absence of effects in other tests:
  No antagonism of pentobarbital-induced sleep
  No antagonism of ptosis and akinesia caused by reserpine
  No modification of righting and stereo-typy caused by apomorphine
  No antagonism of tremor and peripheral signs caused by oxotremorine.

This profile enables the drug according to the invention to be included among substances possessing a dual spectrum: psychostimulatory and antidepressant.

(1) Action of the stimulatory type, characterized by greater toxicity in grouped mice, an increase in motor activity in mice, some stereotyped movement in rats and an antagonism of sodium barbital-induced sleep in mice.

(2) Action of the antidepressant type. The product according to the invention exerts effects in the main tests which reflect antidepressant activity:

Antagonistic action on reserpine-induced hypothermia thermia

Antagonistic action on hypothermia induced by apomorphine (high dose)

Antagonistic action on oxotremorine-induced hypothermia

Slight potentiating action on yohimbine toxicity.

DESCRIPTION OF THE METHODS USED IN PHARMACOLOGY

The pharmacological tests are performed using male rats weighing between 170 and 220 g (Wister strain) and male mice weighing between 18 and 23 g (NMRI strain).

All the experiments are performed blind (the investigator not knowing, when the tests were carried out, which animals had received the substance presumed to be active, and at what dose).

Except where otherwise stated, 10 animals are used per batch.

All the tests are carried out in a laboratory in which the temperature was maintained constant (22°±141° C.).

The administrations are carried out either orally or intraperitoneally.

The injection volumes are 0.5 ml per 100 g of body weight for the rats and 0.25 ml per 20 g of body weight for the mice.

Determination of the acute toxicity in mice

The $LD_{50}$ is determined by the method of Behrens and Karber.

Acute toxicity in isolated mice and in grouped mice

The mice (10 per batch) are placed either individually (toxicity in isolated mice) or grouped in tens (special toxicity) in small boxes 20×10×10 cm.

The mortality is recorded after 1, 2, 3, 4 and 24 hours.

Motor activity in mice

The motor activity is determined using activity cages equipped with photoelectric cells (Boissier and Simon, Arch. Int. Pharmacodyn, 1965, 158, 212-221).

The mice (10 or multiples of 10 per batch) are placed in the activity cage immediately after the administration of the test compounds. The motor activity is measured from the time of placing the animals in the activity cage up to the 60th minute. The counters are read after 30 minutes and then reset to 0 and read every 10 minutes for 30 minutes.

The motility of the animals treated with the different compounds is compared with the motility of a control batch which received distilled water.

Antireserpine activity

At time 0, the mice receive reserpine (2.5 mg/kg) i.p.

4 hours later, when the hypothermia is judged to be sufficiently great (30° to 33° C.), the different test compounds are administered. The rectal temperature is measured every 30 minutes for 2 hours using a probe bearing a thermocouple, inserted to a constant depth. The rectal temperature of the animals treated with the different compounds according to the invention is compared with the temperature of a control batch which received distilled water by the same route as the test compounds.

The akinesia (absence of movement) and ptosis (extent of opening of the pupil, ranging from 0 to 4 according to Rubin et al., 1957) are also scored every 30 minutes for 2 hours.

The products which possess antidepressant activity antagonize the reserpine-induced hypothermia. For each dose of the compound administered, the percentage inhibition of the hypothermia is calculated.

Antiapomorphine activity

At time 0, after the rectal temperatures have become uniform, the mice (6 per batch) are placed in individual boxes(11×3.5×4 cm) which enable them to be observed. 30 minutes later, they receive apomorphine subcutaneously at a dose of 16 mg/kg. The rectal temperature is measured 30 minutes after the apomorphine. The control animals receive distilled water in place of the test compounds. The hypothermia observed in these control animals which have received apomorphine at 16 mg/kg is 33° C. on average. For each dose of compound, the percentage inhibition of the hypothermia is calculated.

Antioxotremorine activity

After the rectal temperatures have become uniform, mice (6 per batch) receive either distilled water or the different test compounds.

30 minutes later, they are administered oxotremorine i.p. at a dose of 0.5 mg/kg.

The mice are then observed: the tremor is scored from 0 to 3 depending on its intensity, and the akinesia is determined according to these criteria: presence or absence, every 10 minutes for 30 minutes.

In addition, the existence of peripheral signs (eyes watering, defecation) is observed for 2 hours. The rectal temperature is measured every 30 minutes for 2 hours after the administration of oxotremorine.

Products which possess antidepressant activity antagonize the oxotremorine-induced hypothermia. Anticholinergic substances antagonize the peripheral signs and the tremor.

For each dose of compound, the percentage of inhibition of the hypothermia is calculated.

Action on yohimbine toxicity

At the time 0, the mice receive either distilled water or the different test compounds. 30 minutes later, they are administered subcutaneously a subtoxic dose of yohimbine hydrochloride at a dose of 25 mg/kg.

The mortality is followed every hour for 4 hours, and then recorded after 24 hours.

The products which possess antidepressant activity cause potentiation of yohimbine toxicity.

Interaction with sodium barbital or with pentobarbital

The animals (6 mice per batch) are placed in individual transparent plastic boxes measuring 20×10×10 cm, and receive the test compounds or distilled water 30 minutes before a hypnotic dose of sodium barbital (180 mg/kg i.p.) or a hypnotic dose of pentobarbital (5 mg/kg i.p.). The times for suppression and reappearance of the righting reflex are noted for each animal.

| | | Psychostimulatory Activity | | | | Antidepressant Activity | | | |
|---|---|---|---|---|---|---|---|---|---|
| | | | | Hypnotic | | Hypothermia | | | Yohimbine |
| Example | Toxicity | Activity measurement | Stereotypy | Barbital antagonism | Pentobar. | Reserpine | Apomorph. | Oxotremor. | toxicity |
| No. 22 | 64 | 0.25 | 4 | 1 (po) | — | 0.25 | 0.5 | — | 0.5 (ip) |
| No. 23 | 256 | 2 | 4 | 4 (po) | — | 2 | 4 (ip-po) | — | 4 (ip) |
| No. 32 | >256 | Mice no effect noted | — | 32 | Potentiation 32 | 1 | 1 | 4 | 2 |

For the 3 products listed below, the different tests enabled the lowest active doses (mg/kg) to be determined, and these are shown in the following table:

II—As regards the nitrile-esters

The product according to the invention posesses a powerful and durable renal vasodilatory action, demonstrated in vitro in the isolated rat kidney and in vivo in anaesthetized (pentobarbital) rats. In the perfused isolated kidney (according to Schmidt and Imbs, J. Cardiovasc. Pharmacol. 2 : 595-605, 1980), the product according to the invention (Example 3) at a concentration of $3 \times 10^{-5}$ M causes a fall in vascular resistance equal to 50% of the vasodilatory action of $10^{-4}$ M papaverine. When administered by intragastric gavage at a dose of 1 mg/kg to anaesthetized rats in which the renal and iliac flowrates (electromagnetic flow measurement) and the AP are measured continuously, the product according to the invention (Example 3) causes a fall in the renal vascular resistance of 35±2% on average (from 42.6±0.7 to 27.8±0.6 mm Hg. min. $ml^{-1}$; m±SEM, n=10), persisting 4 h after the gavage, without any modification of the iliac vascular resistance or the arterial pressure. At doses of 100 or 10 mg/kg (intragastric gavage), the product according to the invention (Example 3) causes a dose dependant iliac vasoconstriction which disappears at a dose of 1 mg/kg.

This activity on the renal vascular bed might be turned to good account in the treatment of acute and chronic renal insufficiency, and also in the long-term treatment of hypertension.

The drugs according to the invention can be administered alone or in combination with other drugs, and in all the usual galenical forms. The form for oral administration is preferable.

The useful daily dose administered orally is between 25 and 250 mg. The galenical form administered will comprise a dose of between 15 and 100 mg, preferably 50 mg.

As emerges from the foregoing, the invention is in no way limited to those modes of implementation, embodiment and application which have been described in greater detail above; on the contrary, it encompasses all the variants thereof which may occur to those versed in the art, without departing from the scope or the range of the present invention.

We claim:

1. A pharmaceutical composition, which comprises as an active ingredient an amount effective for use as a pharmaceutical in the therapy of a host of a cyclized 2,3 diphenyl derivative of γ-nitrile-esters corresponding to the formula C

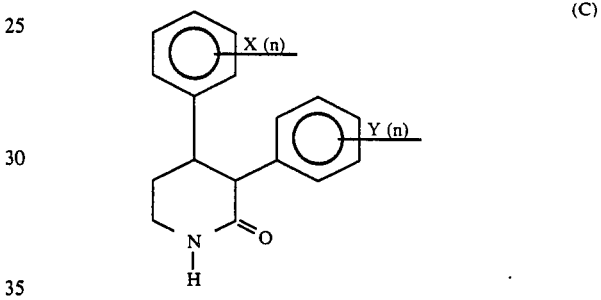

in which, R is a hydrogen atom or a pharmaceutically compatible alkali metal or alkaline-earth metal or a $C_1$-$C_4$ alkyl group, and X or Y which may be identical or different, are a hydrogen or halogen atom or a trifluoromethyl group, $C_1$-$C_4$ alkyl, phenyl, phenyl-($C_1$-$C_4$ alkyl), $C_1$-$C_4$ alkoxy, hydroxy, acyloxy, phenoxy, benzyloxy, $C_1$-$C_4$ alkylsulfonyl or di($C_1$-$C_4$ alkyl)amino group, n being between 1 and 3 in the case where X and/or Y are other than hydrogen, and a pharmaceutically acceptacle carrier.

2. The pharmaceutical composition as claimed in claim 1, in which the products represented by the piperidones of formula C can be in the cis or trans configuration.

3. A method of producing a psychostimulatory or antidepressant effect in a host comprising administering to said host, in an amount effective to produce an antidepressant or psychostimulatory effect, the pharmaceutical composition of claim 1.

4. The method of claim 3 wherein the pharmaceutical composition is administered in a daily dose of from 25 to 250 mg.

5. The method of claim 4 wherein the pharmaceutical composition is administered orally.

* * * * *